//patents.google.com/patent/US12303624B1

United States Patent
Chen et al.

(10) Patent No.: US 12,303,624 B1
(45) Date of Patent: May 20, 2025

(54) THREE-WAY CONNECTING ASSEMBLY AND WEARABLE BREAST PUMP

(71) Applicant: GUANGDONG HORIGEN MOTHER & BABY PRODUCTS CO., LTD., Shantou (CN)

(72) Inventors: Jianbiao Chen, Shantou (CN); Yebin Cai, Shantou (CN); Yongyou Lin, Shantou (CN)

(73) Assignee: Guangdong Horigen Mother & Baby Products Co., Ltd., Shantou (CN)

( * ) Notice: Subject to any disclaimer, the term of this patent is extended or adjusted under 35 U.S.C. 154(b) by 0 days.

(21) Appl. No.: 18/815,209

(22) Filed: Aug. 26, 2024

Related U.S. Application Data (63) Continuation-in-part of application No. PCT/CN2024/098200, filed on Jun. 7, 2024.

(51) Int. Cl.
*A61M 1/06* (2006.01)

(52) U.S. Cl.
CPC .............. *A61M 1/062* (2014.02); *A61M 1/06* (2013.01); *A61M 1/069* (2021.05)

(58) Field of Classification Search
CPC ........ A61M 1/06; A61M 1/062; A61M 1/069; A61M 1/064; A61M 1/067
See application file for complete search history.

(56) References Cited

U.S. PATENT DOCUMENTS

| | | | |
|---|---|---|---|
| 2008/0208116 A1* | 8/2008 | Dao | A61M 1/064 604/74 |
| 2014/0052056 A1* | 2/2014 | Garbez | A61M 1/067 604/74 |
| 2015/0217033 A1* | 8/2015 | Pollen | A61M 1/062 604/74 |

FOREIGN PATENT DOCUMENTS

CN      114767972 A   *   7/2022

* cited by examiner

*Primary Examiner* — Tasnim Mehjabin Ahmed
(74) *Attorney, Agent, or Firm* — Ming Jiang; OPENPTO US LLC (57) ABSTRACT

Provided are a three-way connecting assembly and a wearable breast pump. The three-way connecting assembly includes a three-way connector and an elastic valve plate. The three-way connector is provided with a channel, a milk sucking port, a negative pressure port and a milk outlet. The milk sucking port, the negative pressure port and the milk outlet are spaced apart, and each of the milk sucking port, the negative pressure port and the milk outlet is communicated with the channel. The elastic valve plate is connected with the three-way connector and attached to the milk outlet.

15 Claims, 7 Drawing Sheets

THREE-WAY CONNECTING ASSEMBLY AND WEARABLE BREAST PUMP

CROSS-REFERENCE OF RELATED APPLICATION

This application is a continuation-in-part of PCT application PCT/CN2024/098200 filed on Jun. 7, 2024, which claims priority to Chinese Patent Application No. 202420314935.6, filed on Feb. 20, 2024. All of these applications are herein incorporated by reference in their entireties for all purposes.

TECHNICAL FIELD

The present disclosure relates to the technical field of breast pump, and in particular, it relates to a three-way connecting assembly and a wearable breast pump.

BACKGROUND

With the development of science and technology, wearable breast pumps are welcomed by lactating women, especially working women. The wearable breast pump may be directly worn on a user or integrated onto user's clothes or accessories, so as to release the breast milk accumulated in the breast, thus facilitating collection of the breast milk.

Generally, by setting a valve structure, the breast pump prevents the breast milk from flowing back, and also ensure a suction effect of the breast pump. However, in the related art, the structure of the valve of the breast pump is complicated, and a flow path of discharging the breast milk from a milk outlet is long and has large resistance, thereby resulting in a low milk discharge efficiency.

SUMMARY

Embodiments of the present disclosure provide a three-way connecting assembly and a wearable breast pump, so as to alleviate at least one of the above technical problems.

The embodiments of the present disclosure provides following technical schemes.

In a first aspect, the embodiments of the present disclosure provide a three-way connecting assembly for a wearable breast pump. The three-way connecting assembly includes a three-way connector and an elastic valve plate. The three-way connector is provided with a channel, a milk sucking port, a negative pressure port and a milk outlet. The milk sucking port, the negative pressure port and the milk outlet are spaced apart, and each of the milk sucking port, the negative pressure port and the milk outlet is communicated with the channel. The elastic valve plate is connected with the three-way connector, and attached to the milk outlet. The elastic valve plate and the milk outlet are distributed along a thickness direction of the three-way connector.

In a second aspect, the embodiments of the present disclosure provide a wearable breast pump. The wearable breast pump includes a milk bowl, an airbag, a breast pump flange, a main unit and a three-way connecting assembly. The airbag, the breast pump flange and the main unit are assembled to the milk bowl. The three-way connecting assembly is assembled to the milk bowl, and the three-way connecting assembly includes a three-way connector and an elastic valve plate. The three-way connector is provided with a channel, a milk sucking port, a negative pressure port and a milk outlet. The milk sucking port, the negative pressure port and the milk outlet are spaced apart, and each of the milk sucking port, the negative pressure port and the milk outlet is communicated with the channel. The milk sucking port is communicated with the breast pump flange. The elastic valve plate is connected with the three-way connector and attached to the milk outlet, and the elastic valve plate and the milk outlet are distributed along a thickness direction of the three-way connector. The milk bowl is provided with an air hole and an airbag installation groove, the airbag is installed in the airbag installation groove, and the airbag is located between the milk bowl and the main unit. The air hole is communicated with each of the airbag installation groove and the negative pressure port. When the milk outlet is opened through the elastic valve plate, the milk outlet is communicated with the milk bowl.

BRIEF DESCRIPTION OF THE DRAWINGS

In order to provide clearer explanation of the technical schemes in the embodiments of the present disclosure, drawings required in the description of the embodiments of the present disclosure are simply introduced below. Obviously, the drawings in the description below are only some embodiments of the present disclosure. For those skilled in the art, other drawings may be obtained based on these drawings without creative work.

DETAILED DESCRIPTION OF PREFERRED EMBODIMENTS

In order to make those skilled in the art better understand schemes of the embodiments of the present disclosure, the technical schemes in the embodiments of the present disclosure are described clearly and comprehensively with reference to the drawings in the embodiments of the present disclosure. Obviously, the described embodiments are only a part of the embodiments of the present disclosure, not all embodiments. Based on the embodiments of the present disclosure, all other embodiments obtained by those skilled in the art without creative work belong to a protection scope of the embodiments of the present disclosure.

In the related art, by setting a valve assembly or a valve seat with a valve plate, the breast pump prevents the breast milk from flowing back, and ensures an inflation effect of the breast pump. However, the breast milk needs to flow through the valve assembly or the valve seat, and then the breast milk is discharged from a milk outlet when the valve plate is opened. A flow path of the breast milk is long and has large resistance, thereby resulting in a low milk discharge efficiency.

Figure 1:
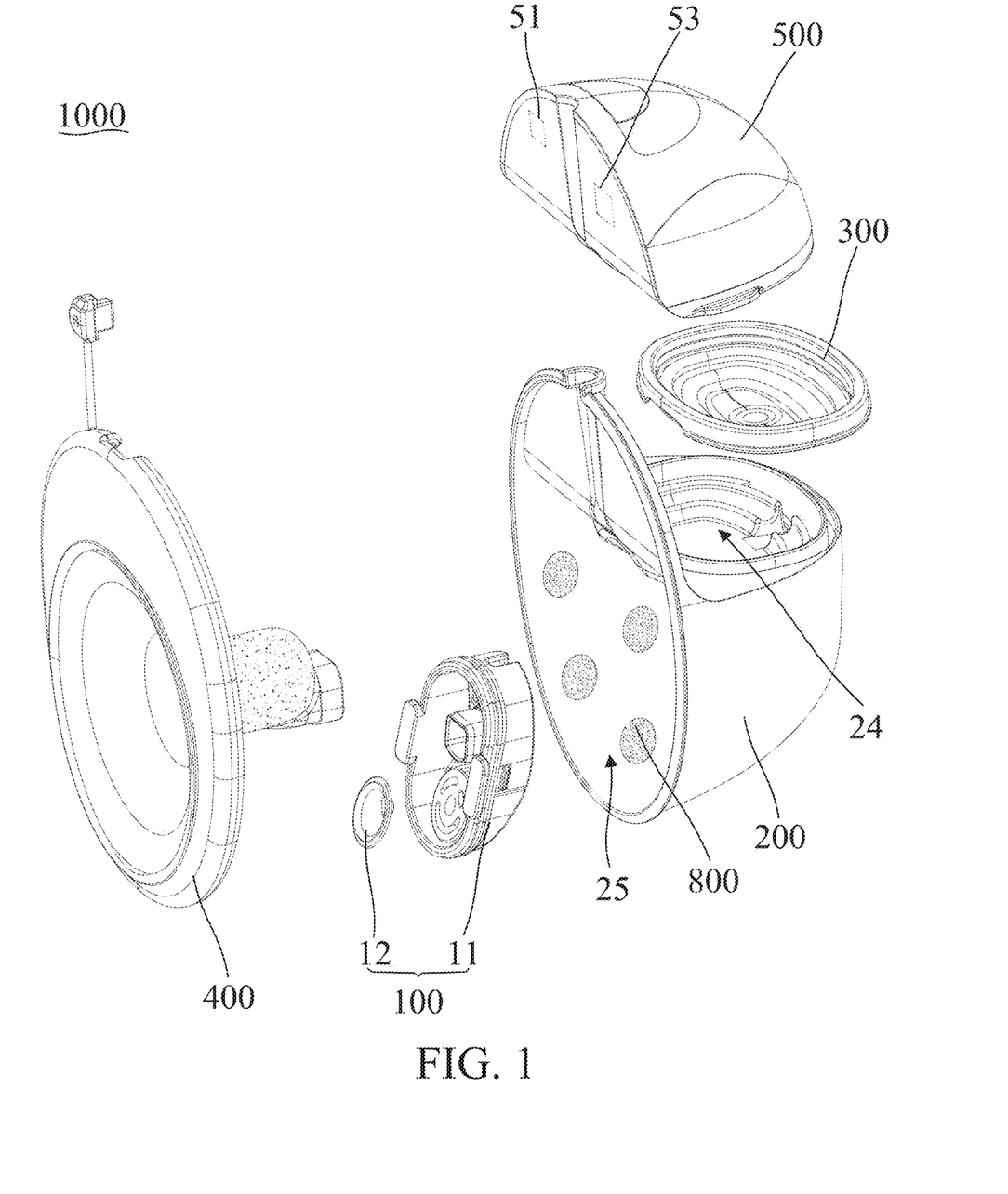
FIG. 1 illustrates a schematic structural diagram of a wearable breast pump provided in the embodiments of the present disclosure.
Figure 2:
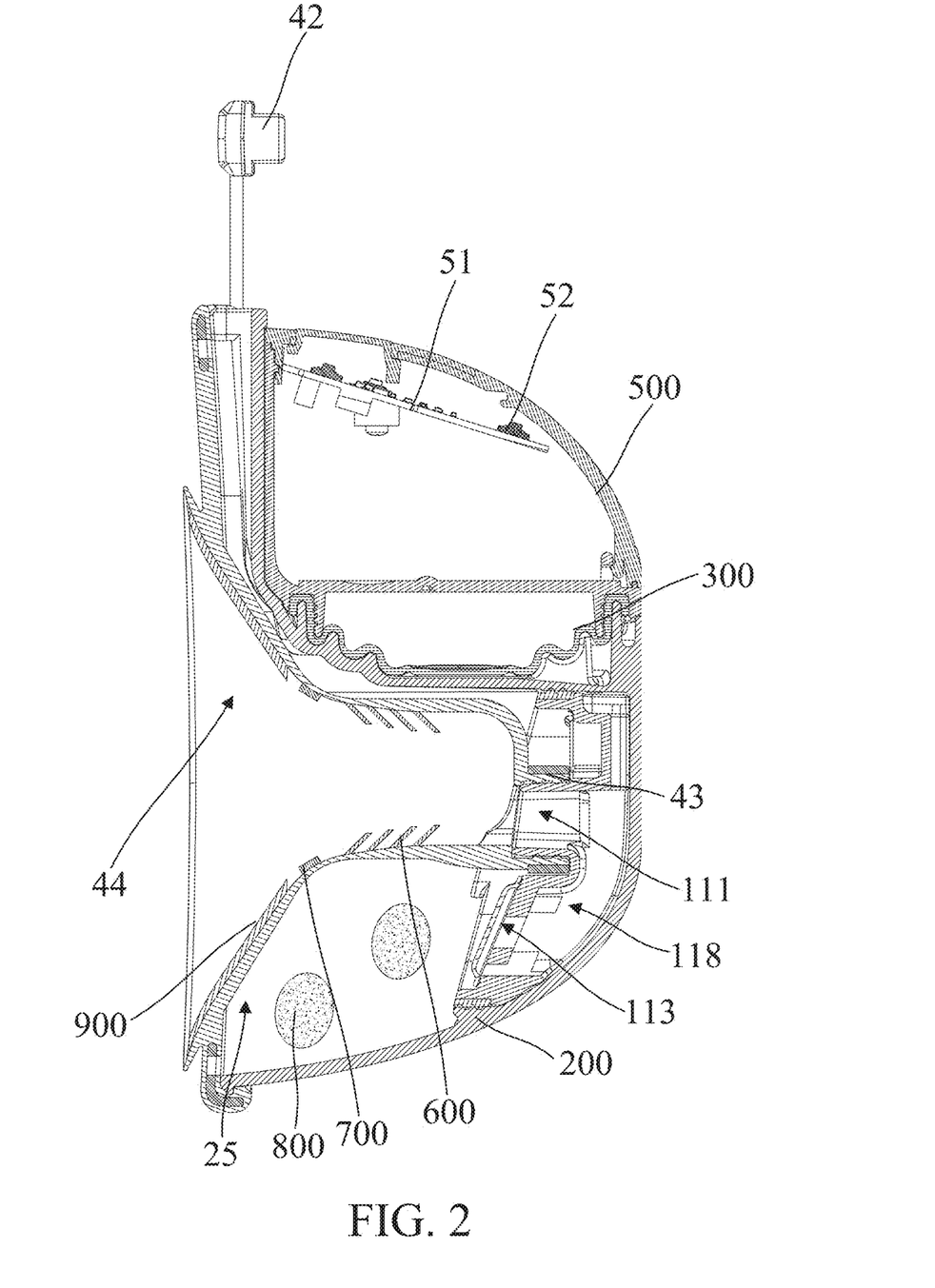
FIG. 2 illustrates a longitudinal sectional view of the wearable breast pump of FIG. 1.

Referring to FIG. 1 and FIG. 2, the embodiments of the present disclosure provide a wearable breast pump 1000.

The wearable breast pump 1000 may be worn on a user's breast without holding the breast pump with the user's hand, which is convenient for the user to use.

In some embodiments, the wearable breast pump 1000 includes a milk bowl 200, an airbag 300, a breast pump flange 400, a main unit 500 and a three-way connecting assembly 100. Each of the airbag 300, the breast pump flange 400, the main unit 500 and the three-way connector 11 is assembled to the milk bowl 200. The airbag 300 may be a flat dish-shaped airbag. The main unit 500 is provided with at least one negative pressure outlet. The airbag 300 is located between the milk bowl 200 and the main unit 500 and covers the negative pressure outlet.

Figure 3:
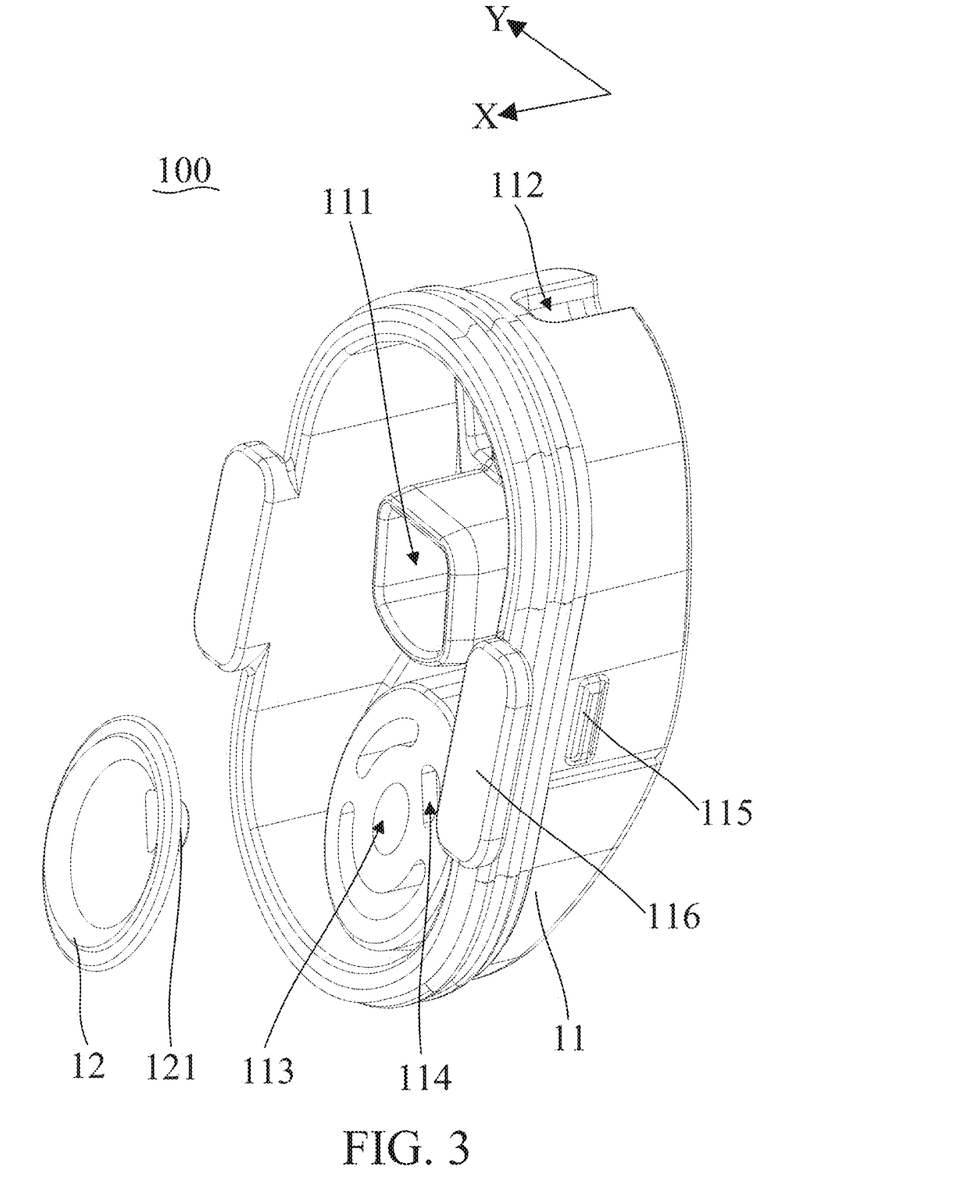
FIG. 3 illustrates a structural schematic diagram of a three-way connecting assembly of FIG. 1.

Referring to FIG. 2 and FIG. 3, in some embodiments, the three-way connecting assembly 100 includes a three-way connector 11 and an elastic valve plate 12. The three-way connector 11 may be in an oval ship form. The three-way connector 11 is provided with a channel 118, a milk sucking port 111, a negative pressure port 112 and a milk outlet 113. The milk sucking port 111, the negative pressure port 112 and the milk outlet 113 are spaced apart, and each of the milk sucking port 111, the negative pressure port 112 and the milk outlet is communicated with the channel 118. As such, the three-way connector 11 can meet needs of the wearable breast pump 1000 for suction, inhalation, and discharge, which is helpful to ensure a normal operation of the wearable breast pump 1000.

In some embodiments, the elastic valve plate 12 is connected with the three-way connector 11 and attached to the milk outlet 113. The elastic valve plate 12 may be elastically deformed and make the milk outlet 113 opened, under pressure of the breast milk. As such, the breast milk in the three-way connector 11 may be discharged from the milk outlet 113 through the opening of the elastic valve plate 12, which is helpful to shorten the flow path of the breast milk in the three-way connecting assembly 100 and reduce the resistance of the breast milk when flowing through the milk outlet 113. Thus, the milk discharge efficiency of the three-way connecting assembly 100 is improved. In addition, the elastic valve plate 12 is attached to the milk outlet 113, so that there is no need to separately provide a valve seat structure for the three-way connecting assembly 100, which is helpful to simplify the structure of the three-way connecting assembly 100 and facilitate manufacturing thereof. When the milk outlet 113 is opened through the elastic valve plate 12, the milk outlet 113 is communicated with the milk bowl 200. For example, the milk outlet 113 is communicated with a milk storage cavity 26 of the milk bowl 200, so as to store the milk discharged from the three-way connector 11.

In some embodiments, the elastic valve plate 12 and the milk outlet 113 are distributed along a thickness direction X of the three-way connector 11. As such, the breast milk flowing under gravity does not directly impact the elastic valve plate 12, and the breast milk may flow to an inner wall of the channel 118 under gravity, and then flow to the milk outlet 113 along the thickness direction X of the three-way connector 11. It is helpful to reduce an influence of the gravity of the breast milk in the three-way connector 11 on an elastic force of the elastic valve plate 12, and it is also helpful to avoid a situation that a superposition of gravity of the breast milk itself and a force of the flowing breast milk has an excessive impact on the elastic valve plate 12. As such, it facilitates reduction of an occurrence of excessive deformation of the elastic valve plate 12, and thus prolonged service life of the elastic valve plate 12.

For example, when the three-way connecting assembly 100 works, the breast milk may enter the three-way connector 11 from the milk sucking port 111 and flow to the milk outlet 113. The breast milk flowing under gravity does not directly impact the elastic valve plate 12. The breast milk may flow to the milk outlet 113 along the thickness direction X of the three-way connector 11, and the elastic valve plate 12 makes the milk outlet 113 opened under the pressure of the breast milk, so that the breast milk is discharged from the milk outlet 113. After the breast milk is discharged from the milk outlet 113, the elastic valve plate 12 may be reset to an initial state under the action of the elastic force, and the elastic valve plate 12 is attached to the milk outlet 113 again, thus closing the milk outlet 113.

In some embodiments, the milk sucking port 111 and the milk outlet 113 have a same orientation. As such, devices of the wearable breast pump 1000 connected with the milk sucking port 111 and the milk outlet 113 may be located at a same side of the three-way connector 11, so that these devices of the wearable breast pump 1000 may be connected with the milk sucking port 111 and the milk outlet 113 from the same side of the three-way connector 11, thus facilitating connections of the three-way connector 11 with other devices.

In some embodiments, one end of the elastic valve plate 12 is provided with a snap-fitting block 121, and the three-way connector 11 is provided with a mount 114. The snap-fitting block 121 is snap-fitted into the mount 114. As such, it is helpful to improve stability of the connection between the elastic valve plate 12 and the three-way connector 11, and reduce loosening of the elastic valve plate 12 from the three-way connector 11. The connection between the elastic valve plate 12 and the three-way connector 11 is simple and convenient to manufacture.

In other embodiments, the end of the elastic valve plate 12 may be connected with the three-way connector 11 in other ways. For example, the end of the elastic valve plate 12 may be connected with the three-way connector 11 by a fastener, which may be set according to actual situations.

In some embodiments, the other end of the elastic valve plate 12 be selectively close to or far away from the milk outlet 113. For example, the other end of the elastic valve plate 12 may be elastically deformed and make the milk outlet 113 opened, under the pressure of the breast milk. For another example, the other end of the elastic valve plate 12 may further be reset to the initial state under the elastic force.

Figure 4:
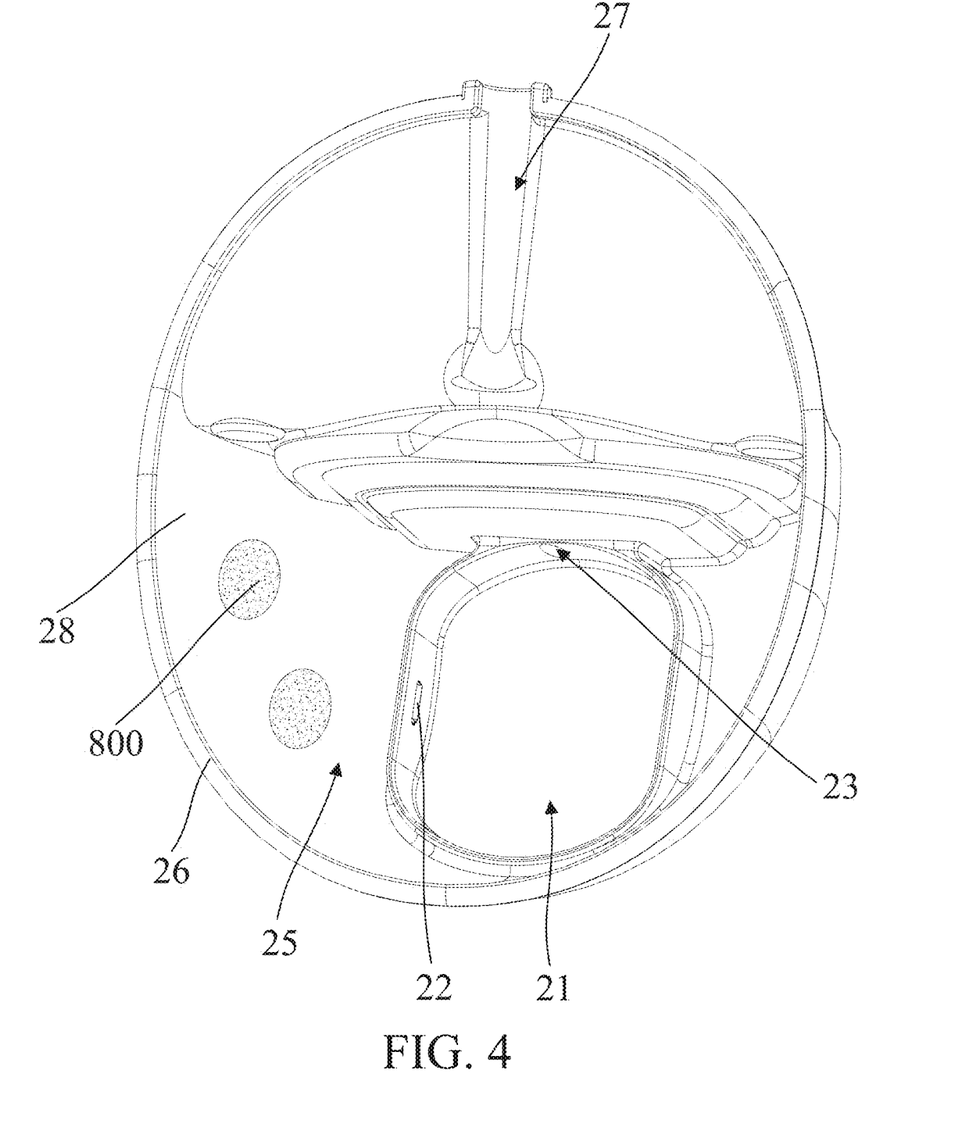
FIG. 4 illustrates a structural schematic diagram of a milk bowl of the wearable breast pump of FIG. 1.

Referring to FIG. 1 and FIG. 4, in some embodiments, the milk bowl 200 may be provided with an air hole 23 and an airbag installation groove 24. The airbag 300 is installed in the airbag installation groove 24, and located between the milk bowl 200 and the main unit 500. The air hole 23 is communicated with each of the airbag installation groove 24 and the negative pressure port 112.

As such, the airbag 300 may inhale and deflate, and change a negative pressure environment in the three-way connector 11 through the air hole 23 and the negative pressure port 112, so that there is a suitable negative pressure environment in the three-way connector 11, which is helpful to ensure that the breast milk can flow into the milk sucking port 111.

Referring to FIG. 2 to FIG. 4, in some embodiments, the milk bowl 200 is provided with a mounting groove 21 and a stud 22. The stud 22 is located in the mounting groove 21, and the three-way connector 11 is provided with a socket 115. The three-way connector 11 is mounted in the mounting groove 21 and the stud 22 is engaged with the socket 115. The stud 22 may be of a bump structure, and the socket 115 may be of a slot structure.

As such, it is helpful to improve the stability of the connection between the three-way connector 11 and the milk bowl 200, thus helping to avoid loosening of the three-way connector 11 from the milk bowl 200. It is further helpful to improve compactness of the connection between the three-way connector 11 and the milk bowl 200, thus facilitating reduction of volume of the wearable breast pump 1000 and convenience for the user to wear it.

In other embodiments, the three-way connector 11 may be connected with the milk bowl 200 in other ways. For example, the three-way connector 11 may be connected with the milk bowl 200 through a fastener, magnetic attraction, etc., which may be set according to the actual situations.

There may be multiple studs 22, and correspondingly, there may be multiple sockets 115. For example, the number of the studs 22 may be two, three, four or more, and the number of sockets 115 may be correspondingly set to two, three, four or more. It is helpful to increase contact area of the connecting structure between the three-way connector 11 and the milk bowl 200, and it is further helpful to better improve the stability of the connection between the three-way connector 11 and the milk bowl 200.

For example, the number of the studs 22 may be two, and the number of sockets 115 may be correspondingly set to two. The two studs 22 are symmetrically arranged on both sides of the milk bowl 200 located in a width direction thereof, and the two sockets 115 are symmetrically arranged on both sides of the three-way connector 11 located in a width direction Y thereof. The two studs 22 are respectively engaged with the two sockets 115, so that the three-way connector 11 may be stably connected with the milk bowl 200.

In some embodiments, the three-way connector 11 may further be provided with a pinch buckle 116, and the pinch buckle 116 is spaced from the socket 115. When the three-way connector 11 is mounted in the mounting groove 21, the pinch buckle 116 is located outside the mounting groove 21 and buckled with the milk bowl 200.

As such, the pinch buckle 116 may be pinched to exert a force on the three-way connector 11, so that the three-way connector 11 may be deformed and embedded in the mounting groove 21. This facilitates pressing of the three-way connector 11 and thus mounting of the three-way connector 11.

There may be two pinch buckles 116, and the two pinch buckles 116 are symmetrically arranged on both sides of the three-way connector 11 located in the width direction Y. As such, the user can press the two pinch buckles 116 to exert a force on the three-way connector 11 from both sides of the three-way connector 11, so that the both sides of the three-way connector 11 may be deformed to better mount the three-way connector 11 in the mounting groove 21.

Figure 5:
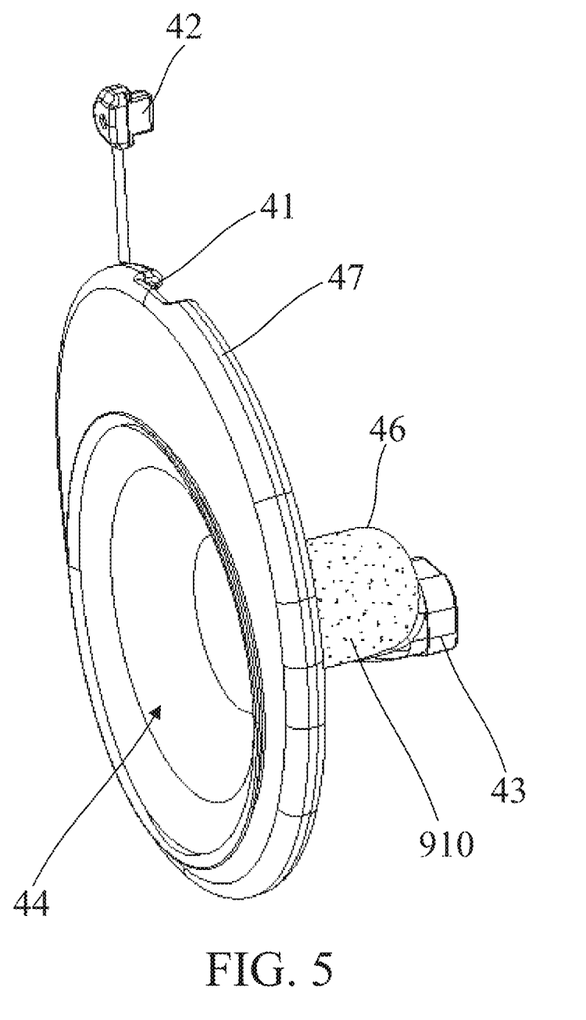
FIG. 5 illustrates a structural schematic diagram of a breast pump flange of the wearable breast pump of FIG. 1.
Figure 6:
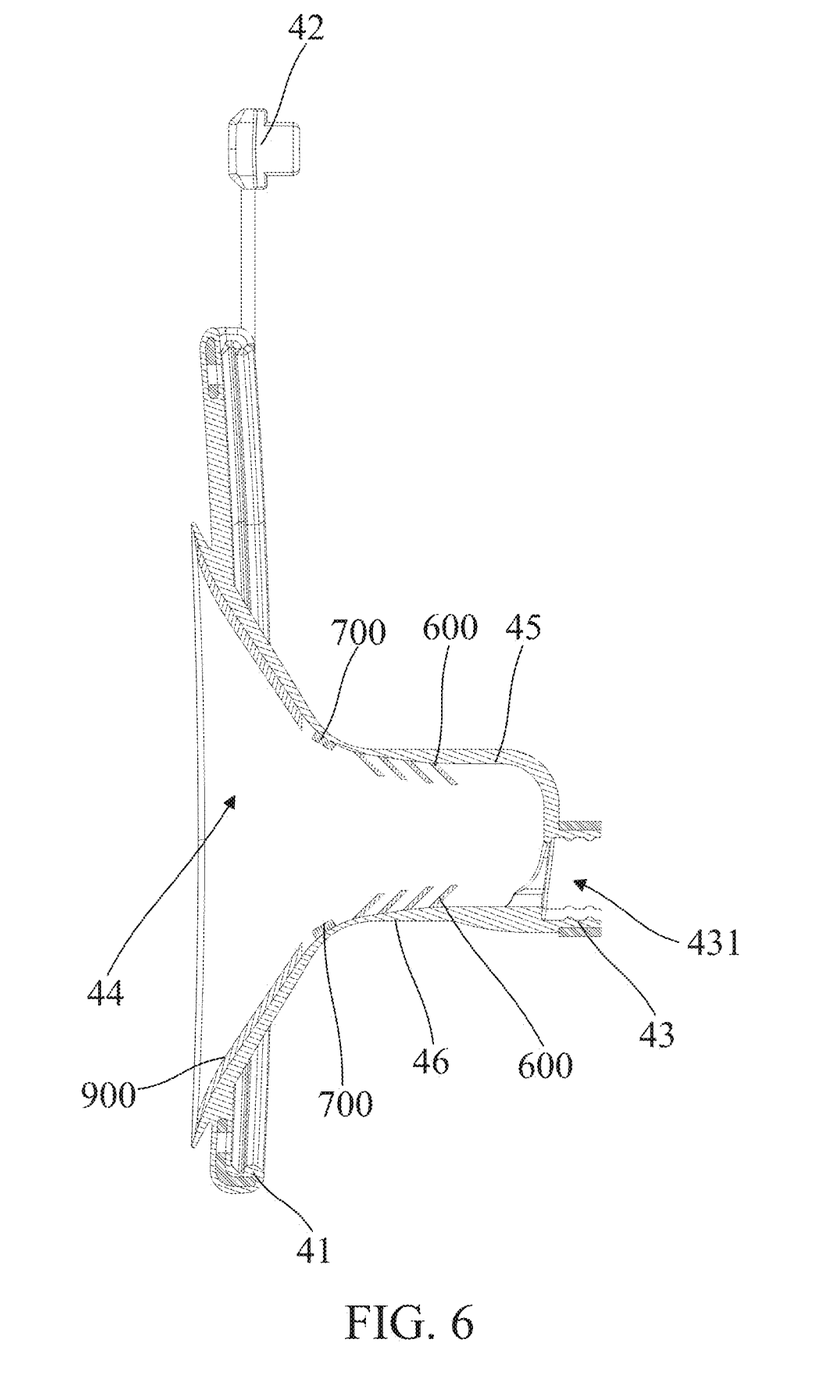
FIG. 6 illustrates a longitudinal sectional view of the breast pump flange of FIG. 5.

Referring to FIG. 4 to FIG. 6, in some embodiments, the breast pump flange 400 may be provided with a positioning pin 43, and the positioning pin 43 is inserted into and communicated with the milk sucking port 111. The milk sucking port 111 is communicated with the breast pump flange 400. For example, the positioning pin 43 may be provided with a connecting channel 431, the connecting channel 431 is communicated with the milk sucking port 111, and the breast milk in the breast pump flange 400 may flow through the connecting channel 431 to the milk sucking port 111. As such, the positioning pin 43 helps to locate a connection position between the breast pump flange 400 and the three-way connector 11, thus improving the connection accuracy of the breast pump flange 400 and the three-way connector 11. It is helpful to improve assembly efficiencies of the breast pump flange 400 and the three-way connector 11. The positioning pin 43 further helps to improve the stability of the connection between the breast pump flange 400 and the three-way connector 11, and helps to avoid disconnection of the breast pump flange 400 with the three-way connector 11.

In some embodiments, the breast pump flange 400 may be provided with a sealing part 41, and the sealing part 41 is arranged along a circumferential edge 47 of the breast pump flange 400. The milk bowl 200 is provided with a milk storage cavity 25 and a sealing fit part 26, and the sealing part 41 is connected with the sealing fit part 26 to seal the milk storage cavity 25.

As such, it is helpful to improve sealing between the milk bowl 200 and the breast pump flange 400, thus helping to avoid overflow of the breast milk from the milk storage cavity 25. It is further helpful to avoid dirty on an appearance surface of the milk bowl 200 because would be caused due to the breast milk adhered to the appearance surface of the milk bowl 200.

Exemplarily, the breast pump flange 400 may be trumpet-shaped, and the breast pump flange 400 may be provided with a breast accommodation cavity 44, and the breast accommodation cavity 44 is communicated with the milk sucking port 111. The sealing part 41 may be located at a side of the breast pump flange 400 away from the breast accommodation cavity 44 and located at an edge of the breast pump flange 400. The sealing part 41 may be a rolled edge flange, and the sealing part 41 may extend inward from the edge of the breast pump flange 400. The sealing fit part 26 may be a rolled edge slot, and the sealing fit part 26 extends inward from the edge of the milk bowl 200. As such, the sealing part 41 and the sealing fitting part 26 are helpful to improve the sealing between the milk bowl 200 and the breast pump flange 400, and avoid milk leakage from the milk bowl 200.

In some embodiments, the milk bowl 200 may be provided with a diversion trench 27, and the milk storage cavity 25 is communicated with the diversion trench 27. As such, the breast milk in the milk storage cavity 25 may be diverted through the diversion trench 27, so as to facilitate pouring of the breast milk. This is helpful to avoid spilling of the breast milk in the milk storage cavity 25 when the breast milk is poured, and reduce a waste of the breast milk.

In some embodiments, the breast pump flange 400 is provided with a cover block 42, and the cover block 42 covers the diversion trench 27. As such, it is helpful to avoid exposure of the breast milk in the milk storage cavity 25 to the outside, and reduce pollution of the breast milk.

Exemplarily, when it is necessary to pour out the breast milk in the milk storage cavity 25, the cover block 42 may be taken off and the breast milk in the milk storage cavity 25 may be poured out through the diversion groove 27. When it is not necessary to pour the breast milk in the milk storage cavity 25, the cover block 42 may be covered on the diversion groove 27, thereby isolating the milk storage cavity 25 from the external environment, and thus reducing the pollution to the breast milk.

In some embodiments, the breast pump flange 400 is a deformable breast pump flange. For example, the breast pump flange 400 may be a silicone breast pump flange, and the silicone breast pump flange may be deformed to better adapt to a shape of the user's breast, which is helpful to improve the user's comfort in using the wearable breast pump 1000.

Referring to FIG. 2 and FIG. 6, in some embodiments, the wearable breast pump 1000 may further include an air cushion 900, the air cushion 900 is attached onto an inner wall 45 of the breast pump flange 400, and located at a side of the breast pump flange 400 away from the milk sucking port 111. As such, the air cushion 900 may be deformed to adapt to different shapes of the user's breast, so that the air cushion 900 may fit the user's breast, which is helpful to provide a more comfortable pumping experience for users.

The breast pump flange 400 may be provided with a support member to support the breast pump flange 400, so that the breast pump flange 400 may maintain a certain shape while deforming, so as to better adapt to the shape of the user's breast.

In some embodiments, the wearable breast pump 1000 further includes a plurality of anti-overflow plates 600, all of the plurality of anti-overflow plates 600 are arranged on and protrude from an inner wall 45 of the breast pump flange 400, and the anti-overflow plates 600 are spaced along an axial direction of the breast pump flange 400. As such, the plurality of anti-overflow plates 600 may reduce backflow of the breast milk from the milk sucking port 111 to the breast pump flange 400, which is helpful to reduce overflow of the breast milk from the breast accommodation cavity 44, so as to reduce a waste of the breast milk. In the case of the plurality of anti-overflow plates 600, when a part of the plurality of anti-overflow plates 600 close to the milk sucking port 111 fail to sufficiently block the breast milk, other anti-overflow plates 600 far away from the milk sucking port 111 may further block the breast milk, thus better reducing the overflow of the breast milk from the breast accommodation cavity 44.

In some embodiments, as illustrated in FIG. 6, the part of the anti-overflow plates 600 away from the milk sucking port 111 are tilted in a direction facing toward the milk sucking port 111, or each of the anti-overflow plates 600 is tilted in the direction facing toward the milk sucking port 111. As such, by tilting the anti-overflow plate 600 in the direction facing toward the milk sucking port 111, it is helpful to divert the breast milk in the breast pump flange 400, so that the breast milk in the breast pump flange 400 may flow to the milk sucking port 111 in a predetermined direction.

Figure 7:
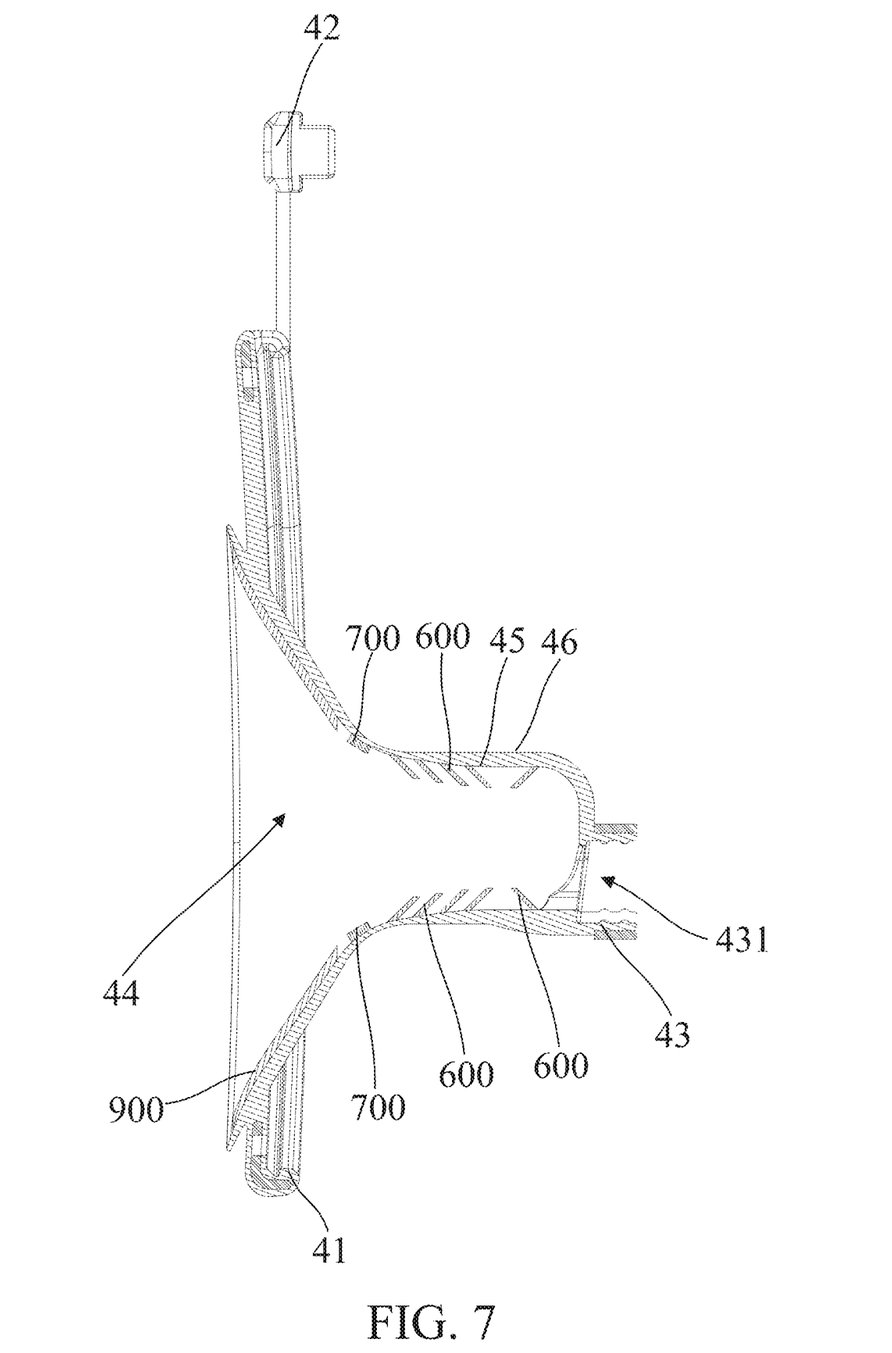
FIG. 7 illustrates a longitudinal sectional view of another breast pump provided in the embodiments of the present disclosure.

In some embodiments, as illustrated in FIG. 7, a part of the anti-overflow plates 600 close to the milk sucking port 111 are tilted in a direction away from the milk sucking port 111. As such, the breast pump flange 400 may have, at a position near the milk sucking port 111, a large space to contain the breast milk, which is helpful to improve an anti-overflow effect of the anti-overflow plate 600.

In some embodiments, the wearable breast pump 1000 further includes a vibrating massager 700, and the vibrating massager 700 is assembled in the breast pump flange 400 and located near the anti-overflow plates 600. For example, the vibrating massager 700 is arranged on the inner wall 45 of the breast pump flange 400 and spaced from the plurality of anti-overflow plates 600. As such, the vibrating massager 700 may give, through vibration, a massage on the breast to imitate a sucking action of a baby, which is helpful to stimulate the breast to promote secretion of the breast milk and reduce breast blockage. In addition, the vibrating massager 700 may transmit the vibration to the anti-overflow plates 600, which enables the anti-overflow plate 600 protruding from the inner wall 45 of the breast pump flange 400 to transmit the vibration to a skin surface of the breast, so as to better stimulate the breast and further promote the secretion of the breast milk.

In some embodiments, the wearable breast pump 1000 may further include an electric heating element 800, and the electric heating element 800 is attached onto an inner wall 28 of the milk bowl 200 and located in the milk storage cavity 25. The electric heating element 800 may be an electric heating film.

As such, the electric heating element 800 may heat the inner wall 28 of the milk bowl 200 and the breast milk in the milk storage cavity 25, so that the breast milk in both the milk bowl 200 and the milk storage cavity 25 may be maintained at a proper temperature, which is helpful to reduce nutrient loss of the breast milk, and facilitates direct feeding by the user or storage.

There may be multiple electric heating element 800. For example, the number of the electric heating elements 800 may be two, three, four or more. This helps to increase heating area of the electric heating elements 800. Alternatively, the electric heating element 800 may cover the inner wall 28 of the milk bowl 200, in such a manner that the electric heating element 800 is arranged on the whole of the inner wall 28 of the milk bowl 200, thus better improving the heating effect of the electric heating elements 800 on the inner wall 28 of the milk bowl 200. It further helps to ensure consistency of the temperature of the inner wall 28 of the milk bowl 200, so as to reduce deterioration of the breast milk that would be caused by excessive temperature difference of the breast milk in the milk bowl 200.

In some embodiments, the wearable breast pump 1000 may further include an annular heating film 910, and the annular heating film 910 is attached onto the breast pump flange 400 and extends along the axial direction of the breast pump flange 400.

As such, the annular heating film 910 may heat the breast pump flange 400, so that the breast pump flange 400 may be maintained at a proper temperature. It is helpful to improve breast comfort when the user wears the wearable breast pump 1000. It further helps to ensure that the breast milk flowing through the breast pump flange 400 may be maintained at the proper temperature, which facilitates reduction of the nutrient loss of the breast milk, and improves a flow speed of the breast milk.

In some embodiments, the annular heating film 910 is located on an outer circumferential surface 46 of the breast pump flange 400. As such, it is helpful to reduce burn injuries to the user that would be caused due to direct contact between the annular heating film 910 and the user's breast, and it is further helpful to reduce a thermal influence of the annular heating film 910 on the vibrating massager 700. The annular heating film 910 may be located at a different side of the breast pump flange 400 from the anti-overflow plate 600 and the vibrating massager 700, so that the outer circumferential surface 46 of the breast pump flange 400 may have large area to arrange the annular heating film 910.

In some embodiments, the milk bowl 200 is transparent, and an outer surface of the milk bowl 200 is provided with a capacity scale. As such, the milk bowl 200 may be integrated with milk storage function and metering function. It is helpful for the user to intuitively know an amount of breast milk in the milk bowl 200, which is convenient for the user to selectively, according to the amount of breast milk, replenish the breast milk into the milk bowl 200 or pour out the breast milk in the milk bowl 200.

In some embodiments, the main unit 500 may include a power supply 51, a controller 52 and a vacuum pump 53. The controller 52 is electrically connected with the power supply 51, the controller 52 communicates with the vacuum pump 53 through signal, and the vacuum pump 53 is connected with the airbag 300.

As such, the controller 52 may control the vacuum pump 53 to work, and there is no need for the user to manually operate the vacuum pump 53, which is helpful for the user to use the wearable breast pump 1000 conveniently.

When it is necessary to pump the breast milk, the breast pump flange 400 is placed on the breast, and the controller 52 controls the vacuum pump 53 to vacuum the airbag 300, so that the negative pressure is generated in the breast pump flange 400 to pump the breast milk.

In the embodiments of the present disclosure, unless otherwise specified or limited, the term "assembly" and other terms shall be broadly understood. For example, it may be a fixed connection, a detachable connection or an integral connection; it may be a mechanical connection; it may be directly connected, indirectly connected through an intermediary, or internally communicated between two elements; it may be only in surface contact, or connected through surface contact of an intermediate medium. For those skilled in the art, the specific meanings of the terms above in the embodiments of the present disclosure may be understood according to specific situations.

In addition, the terms "first" and "second" are only used for distinguishing descriptions, which cannot be understood as specific or special structures. The description of the term "some embodiments" means that a specific feature, structure, material or characteristic described in connection with the embodiment or example is included in at least one embodiment or example of the present disclosure. In the embodiments of the present disclosure, schematic expressions of the terms above are not necessarily aimed at the same embodiments or examples. Moreover, the specific features, structures, materials or characteristics described may be combined in any one or more embodiments or examples in a suitable manner. In addition, without contradicting each other, those skilled in the art may combine and associate different embodiments or examples described in the embodiments of the present disclosure, and combine and associate features of different embodiments or examples described in the embodiments of the present disclosure.

The embodiments above are only used to illustrate the technical schemes of the embodiments of the present disclosure, but not to limit it. Although the embodiments of the present disclosure are described in detail with reference to the aforementioned embodiments, it is understandable for those skilled in the art that they may still modify the technical schemes recorded in the embodiments mentioned above, or replace some technical features with equivalents. These modifications or replacements do not make an essence of the corresponding technical schemes deviate from a spirit and scope of the technical schemes of various embodiments of the present disclosure, and they shall be included in a protection scope of the embodiments of the present disclosure.

What is claimed is:

1. A wearable breast pump, comprising:
    a milk bowl, an airbag, a breast pump flange, and a main unit, wherein each of the airbag, the breast pump flange and the main unit is assembled to the milk bowl; and
    a three-way connecting assembly, wherein the three-way connecting assembly is assembled to the milk bowl, and the three-way connecting assembly comprises a three-way connector and an elastic valve plate;
    the three-way connector is provided with a channel, a milk sucking port, a negative pressure port and a milk outlet, the milk sucking port, the negative pressure port and the milk outlet are spaced apart, each of the milk sucking port, the negative pressure port and the milk outlet is communicated with the channel, and the milk sucking port is communicated with the breast pump flange;
    the elastic valve plate is connected with the three-way connector and attached to the milk outlet, and the elastic valve plate and the milk outlet are distributed along a thickness direction of the three-way connector; and
    the milk bowl is provided with an air hole and an airbag installation groove, the airbag is installed in the airbag installation groove and located between the milk bowl and the main unit, the air hole is communicated with each of the airbag installation groove and the negative pressure port, and when the milk outlet is opened through the elastic valve plate, the milk outlet is communicated with the milk bowl.

2. The wearable breast pump of claim 1, wherein the milk sucking port and the milk outlet have a same orientation.

3. The wearable breast pump of claim 1, wherein one end of the elastic valve plate is provided with a snap-fitting block, the three-way connector is further provided with a mount, and the snap-fitting block is snap-fitted into the mount; the other end of the elastic valve plate is configured to selectively be close to or far away from the milk outlet.

4. The wearable breast pump of claim 1, wherein the milk bowl is provided with a mounting groove and a stud, the stud is located in the mounting groove;
    the three-way connector is further provided with a socket, the three-way connector is mounted in the mounting groove, and the stud is engaged with the socket.

5. The wearable breast pump of claim 4, wherein the three-way connector is further provided with a pinch buckle, the pinch buckle is spaced from the socket, and when the three-way connector is mounted in the mounting groove, the pinch buckle is located outside the mounting groove and buckled with the milk bowl.

6. The wearable breast pump of claim 1, wherein the breast pump flange is provided with a positioning pin, the positioning pin is inserted into the milk sucking port, the positioning pin is provided with a connecting channel, and the connecting channel is communicated with the milk sucking port.

7. The wearable breast pump of claim 1, wherein the breast pump flange is provided with a sealing part, and the sealing part is arranged along a circumferential edge of the breast pump flange;
    the milk bowl is provided with a milk storage cavity and a sealing fit part, and the sealing part is connected with the sealing fit part to seal the milk storage cavity.

8. The wearable breast pump of claim 1, wherein the milk bowl is provided with a diversion trench and a milk storage cavity, the milk storage cavity is communicated with the diversion trench;
    the breast pump flange is provided with a cover block, and the cover block covers the diversion trench.

9. The wearable breast pump of claim 1, wherein the wearable breast pump further comprises an air cushion, the air cushion is attached onto an inner wall of the breast pump flange, and the air cushion is located at a side of the breast pump flange away from the milk sucking port.

10. The wearable breast pump of claim 1, wherein the wearable breast pump further comprises a plurality of anti-overflow plates, the plurality of anti-overflow plates are all arranged on and protrude from an inner wall of the breast pump flange, and the plurality of anti-overflow plates are spaced along an axial direction of the breast pump flange;

a part of the plurality of anti-overflow plates away from the milk sucking port are tilted in a direction facing toward the milk sucking port, or a part of the plurality of anti-overflow plates close to the milk sucking port are tilted in a direction away from the milk sucking port, or each of the plurality of anti-overflow plates is tilted in the direction facing toward the milk sucking port.

11. The wearable breast pump of claim 10, wherein the wearable breast pump further comprises a vibrating massager, the vibrating massager is assembled in the breast pump flange and located near the plurality of anti-overflow plates.

12. The wearable breast pump of claim 1, wherein the wearable breast pump further comprises an electric heating element, the milk bowl is provided with a milk storage cavity, and the electric heating element is attached onto an inner wall of the milk bowl and located in the milk storage cavity.

13. The wearable breast pump of claim 1, wherein the wearable breast pump further comprises an annular heating film, the annular heating film is attached onto the breast pump flange and extends along an axial direction of the breast pump flange, and the annular heating film is located on an outer circumferential surface of the breast pump flange.

14. The wearable breast pump of claim 1, wherein the milk bowl is transparent, and an outer surface of the milk bowl is provided with a capacity scale.

15. The wearable breast pump of claim 1, wherein the main unit comprises a power supply, a controller and a vacuum pump, the controller is electrically connected with the power supply, the controller is configured to communicate with the vacuum pump through signal, and the vacuum pump is connected with the airbag.

* * * * *